(12) United States Patent
Nazeri

(10) Patent No.: US 7,286,865 B2
(45) Date of Patent: Oct. 23, 2007

(54) EKG RECORDING ACCESSORY SYSTEM (EKG RAS)

(76) Inventor: Alireza Nazeri, 1510 Shoreclub Dr., St. Claire Shores, MI (US) 48080-1550

( * ) Notice: Subject to any disclaimer, the term of this patent is extended or adjusted under 35 U.S.C. 154(b) by 0 days.

(21) Appl. No.: 11/369,315

(22) Filed: Mar. 6, 2006

(65) Prior Publication Data

US 2006/0167353 A1   Jul. 27, 2006

Related U.S. Application Data

(62) Division of application No. 10/719,604, filed on Nov. 21, 2003.

(60) Provisional application No. 60/452,483, filed on Mar. 4, 2003.

(51) Int. Cl.
*A61B 5/04* (2006.01)

(52) U.S. Cl. .................. 600/382; 600/386; 600/391; 600/392; 600/393

(58) Field of Classification Search ............. 600/382, 600/390–393
See application file for complete search history.

(56) References Cited

U.S. PATENT DOCUMENTS

| 4,583,549 | A | * | 4/1986 | Manoli | 600/391 |
|---|---|---|---|---|---|
| 4,763,660 | A | * | 8/1988 | Kroll et al. | 600/391 |
| 5,370,116 | A | * | 12/1994 | Rollman et al. | 600/382 |
| 6,219,568 | B1 | * | 4/2001 | Kelly et al. | 600/386 |
| 6,259,939 | B1 | * | 7/2001 | Rogel | 600/390 |
| 6,385,473 | B1 | * | 5/2002 | Haines et al. | 600/393 |
| 6,560,473 | B2 | * | 5/2003 | Dominguez | 600/382 |
| 6,643,541 | B2 | * | 11/2003 | Mok et al. | 600/546 |
| 6,847,836 | B1 | * | 1/2005 | Sujdak | 600/382 |
| 2002/0133069 | A1 | * | 9/2002 | Roberts | 600/382 |

* cited by examiner

*Primary Examiner*—Lee S. Cohen
(74) *Attorney, Agent, or Firm*—Robert L. Shaver; Dykas, Shaver & Nipper, LLP

(57) ABSTRACT

The invention is a precordial pad for positioning EKG electrodes on a patient for anatomically correct and repeatable placement. Data can be transmitted from the EKG pad of the invention by wire or wireless means. The pad includes a sizing aid, and a positioning device. The invention is also a system for obtaining and sending EKG data.

22 Claims, 11 Drawing Sheets

EKG RECORDING ACCESSORY SYSTEM (EKG RAS)

PRIORITY

This application is a Divisional application and claims the priority date of the utility application entitled EKG Recording Accessory System (EKG RAS) filed by Alireza Nazeri on Nov. 21, 2003, with Ser. No. 10/719,604, which claims the priority date of the provisional application entitled EKG Recording Accessory System (EKG RAS) filed by Alireza Nazeri on Mar. 4, 2003, with Ser. No. 60/452,483, the disclosure of which is incorporated herein.

DESCRIPTION

BACKGROUND OF THE INVENTION

1. Field of the Invention

The present invention generally relates to an EKG contact electrode pad, and more particularly relates to EKG contact pads with temperature sensors, sizing selection, and placing means.

2. Background Information

Electrocardiography (EKG, ECG) is a medical test for recording the electrical activity of the heart. In the standard twelve lead EKG there are twelve (12) different wires that carry electrical signals from the area of the body to which they are attached. Certain leads are attached to the person's chest in six standard areas. These are known as precordial leads. Four of the twelve leads are the four limb electrodes: right wrist, left wrist, right ankle and left ankle. In some cases, the placing of two extra lead electrodes in the right side of the patient's chest allows the possibility to record the EKG of the right heart. The limb leads are designated RL, RF, LL, and LF, and attach respectively to the two ankles and the two wrists of the patient. The precordial leads are designated as V1, V2, V3, V4, V5, and V6, and the leads for the right side of the heart are designated VR1 and VR2. The limb leads can be placed in an "adjusted" position, rather than on the extremities. The adjusted position for the limb leads are on the torso of the patient.

From the time of the invention of EKG to present usage, each electrode is generally connected separately to the EKG recorder by wire. This means that, for the routine twelve lead EKG, we need at least ten (10) separate electrodes attached to standard anatomical positions and ten (10) wires that go separately to the EKG machine. In the configurations including the right heart EKG, they will become twelve (12) separate electrodes. These standard electrode placements can also be used for electrodes for an external pacemaker, a defibrillation device, and for real time heart monitoring of the patients in critical care units.

The results of the EKG will be printed as a graph on standard paper or shown on the monitor. EKG is the most commonly used diagnostic test in medicine for evaluating the function of the heart. Reading the EKG is very important in patient management, as the difference between a normal and an abnormal reading can be measured in millimeters on the chart. Correct placement of electrodes in the standard positions, attachment to the skin, perfect conductivity, and the least artifacts as possible in the recording are the keys in the repeatability, accuracy, and reliability of this procedure. For the best performance, a skilled physician or technician should place the electrodes. With the currently available methods of electrode placement, there can be significant errors produced in the EKG recordings. For example, one person may place the electrodes in a different position than another person, and the same person can place them in another position at a different time. Even if placed predictability, it could be placed in a wrong anatomical position.

Thus, in the conventional placement of the electrodes, the repeatability, accuracy, and reliability of the data are suspect, especially in emergency situations when procedures are carried out rapidly and in difficult situations.

Therefore, what is needed are repeatability, consistency, and accuracy in the placement of electrodes for an EKG recording on the same patient with different users, or on different patients by the same user.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

These objects, as well as others, are accomplished by the EKG pad of the invention. The repeatability is provided by an array of electrodes that are mounted in a disposable precordial pad. The precordial pad of the invention has an array of EKG electrodes and a temperature sensor distributed on a flexible, multi-layer material. The flexible material forms a pad body, which has an outer surface and a body surface. The body surface of the precordial pad body includes an adhesive layer, which stabilizes the pad on a person's torso and ensures that the readings are taken during a test from one, and only one, position on the patient's chest. The adhesive layer of the precordial pad is covered until it is ready for use. The precordial pad is covered by an adhesive cover, which is stripped off to expose the adhesive surface when the pad is ready to be used. The body surface also includes conductive electrodes and a temperature sensor, which will contact the patient's skin.

The pad also has a middle layer, which is the main circuit layer. The circuit layer includes a printed circuit that collects all data from all applicable electrodes, sensors, and attachments of the pad and brings them to the one area on the outer surface of the pad. The circuit layer is designed and made to be capable of tolerating higher voltages that may be used for defibrillation. The printed circuit can be made of copper, conductive ink, or other electrically conductive material.

The outer surface pad also includes a signal export area. This is where the data-transmitting module attaches to the pad and carries all of the signals from one point to the EKG machine. The signal export module can be a wireless transmitter that transmits data from the precordial pad to the EKG machine via the system adaptor. The module is also capable of transmitting data via a conventional wiring harness, as single cable includes a bundle of wires leaving the main precordial pad to a designed universal adaptor of the invention, which is connected to an EKG machine.

The invention is also a system for taking the EKG of a patient, which has a capability of performing defibrillation, external pacing, and monitoring the patient's heart at the same time and with the same precordial pad. The system includes a disposable EKG precordial pad as described above, as well as some additional components. The additional components include a measuring device, which is used to measure the size of the patient's test area such as his chest or torso. Depending on the size of the patient's test area, a size of precordial pad is selected based on the testing system of the invention. For instance, sizes 1, 2, 3, and 4 may be available for various sizes of patients. Sizing can also include consideration for gender, as pads for males are likely to be larger than those for females. Pad sizes can also be designated as Small, Medium, Large, Extra Large, etc. Other designations are obviously possible and would be related to an indication on the measuring device of the invention. The correct size of the pad can also be determined based on the patient's gender and shirt size.

The system includes a positioning device, which can be used to measure a patient for pad size, as well as aid the caregiver in positioning a pad correctly on a patient. The positioning device of the system is used with the well-known anatomical marker on the human chest called the Supra Sternal Notch. By placing a curved edge of the positioning device on the patient's supra sternal notch, the precordial pad can be placed accurately and consistently in the anatomically correct position, with the electrodes thus placed correctly. This feature allows non-professional users to place the EKG electrodes on themselves with high accuracy. This has not been possible with EKG electrodes in the prior art.

The pad is also composed of materials to be translucent to the X-Ray so patients can wear the pad while they are being x-rayed. The pad is also designed and composed of materials to be water resistant and waterproof. The pad is also from biocompatible material to make the least allergic reaction for the patients. The pad may also be worn while the patient is getting an MRI.

The Signal Export Module is another part of this system. This has an interface for connection to the signal export area of the pad. The signal export module receives signals from the related electrodes and sensors. It can include a connection site for connection of a single cable, which can be used to transmit the data to the universal adaptor. The cable can be regular wire or fiber optic. The module also can contain a micro-transmitter to transmit data wirelessly to the universal adaptor. This will have the benefit of wireless transmission and can utilize bluetooth, infrared, wi-fi, or other wireless technologies. One way to select between wireless and wired transmission is to activate the wireless mode, unless a cable is connected to the module. It would typically have a rechargeable long life lithium battery, or another suitable battery type. The signal export module can also have a data recognition sensor to sense the EKG signals and send an alarm if the patient has certain preprogrammed changes in his or her EKG, such as arrhythmias. The wireless feature of the pad allows the patient to wear the pad, put the module on wireless mode, and be able to move around, go to the bathroom, go to the lunchroom, move in a wheelchair, etc. The pattern recognition ability of the system will automatically send an alarm signal if an abnormal event happens.

The Universal Adaptor/Receiver is another part of the invention. Its features will include compatibility with all of the current or future EKG recorders in the market. It includes an input site for the wires from the recorder and a site for connection of the wires from the pad and limb electrodes. This part will be used for the wire transmission of data from the pad to the EKG machine. The adaptor/receiver also contains a receiver for receiving data wirelessly from the micro-transmitter and transferring them to the recorder. It also includes a digital display to show body temperature. A switch will allow the adaptor/receiver to select wire or wireless transmission mode, and to change output to the selected format for the EKG machine in use, or for a defibrillator, external heart pacing system, or for real time monitoring.

The pad is disposable so that it will be used for only one patient. This will limit the risk of transmitting skin disorders from one person to another, which is a concern in the currently available method.

An important feature of the pad is that the electrodes embedded in the pad extend from the pad surface for better contact. Rather than being flush with the pad, the electrode layer of the pad includes a device that causes the electrodes to extend away from the pad by two to five millimeters. The electrode-extending device would also exert a small amount of pressure so that when the pad is attached to the patient's chest, the extended electrodes press harder against the patient's skin than they would otherwise. The electrode extension device can be some type of biased device, such as a coiled spring or some other type of spring. The electrode extension device can also be a biased member made of foam. The foam structure would be compressed under the electrode when the adhesive cover is applied. When the adhesive cover is removed, the compressed foam would force the electrode to extend out from the body surface of the pad by two to five millimeters or more, preferably.

A foam pad or other biased device would also apply the correct pressure that would be transmitted to the electrode and thus, to the patient's skin. This will produce the highest quality contact and conductivity, which is directly related to the performance of the recording.

The body surface of the pad includes an adhesive layer made from biocompatible and non-allergic materials. This will be attached to the skin upon removal of the cover. Another feature of the invention is that the electrodes may be pre-coated with a transmitting gel, which would be sandwiched between the electrode and the cover of the adhesive layer. When the adhesive cover is removed, the transmitting gel would remain on the electrode contact surface and be available to improve the connection between the electrode and the patient's skin. All of these features result in a precordial pad that can improve the repeatability of test results, which can stabilize the pad during a particular test, which can read low temperatures and send that information to the EKG machine, and which facilitates rapid, accurate, and repeatable placement of the precordial pad of the invention. This pre-application of gel also eliminates a possible route of cross contamination.

The precordial pad of the invention also includes a temperature sensor built into the pad body. The temperature sensor measures a low range of body temperatures. It is when a patient's body temperature is in a low range that the electrical pattern of the heart will be affected. Knowing this factor in the recording is key to distinguishing the pattern of a normal from an abnormal EKG, as an EKG taken from a patient who is at a below normal temperature will have altered the readings. If that EKG is reviewed at a later time, a full interpretation of the EKG readings would not be possible without knowledge of the patient's temperature at the time the reading was taken. For that reason, a temperature sensor is built into the pad body. The temperature sensor would also be linked to the data-transmitting module, and sent to the EKG machine for recording with other data.

The micro-transmitter for the limb electrodes uses the same technology for the four electrodes of the limb leads. This can be associated with each single electrode for wireless transmission, if applicable.

Added features of the precordial pad of the invention are connection points to the four limb electrodes. These sensing sites are on the four limbs of the patient, including the right arm, left arm, the right ankle, and the left ankle, or their adjusted positions on the chest of the patient. The designed sets of limb electrodes of this invention are also capable of attachment on the chest, rather than on the limb, to simplify the installation of electrodes for EKG test if the user chooses. The pad body of the invention would include sites to allow electrodes from the four limbs to connect to the pad body and be routed with the information from the other electrodes of the pad body to the EKG machine.

Further, the purpose of the foregoing abstract is to enable the United States Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measure by the claims, nor is it intended to be limiting as to the scope of the invention in any way.

Still other objects and advantages of the present invention will become readily apparent to those skilled in this art from the following detailed description, wherein I have shown and described only the preferred embodiment of the invention, simply by way of illustration of the best mode contemplated by carrying out my invention. As will be realized, the invention is capable of modifications in various obvious respects all without departing from the invention. Accordingly, the drawings and description of the preferred embodiment are to be regarded as illustrative in nature, and not as restrictive in nature.

DESCRIPTION OF THE PREFERRED EMBODIMENTS

Figure 1:
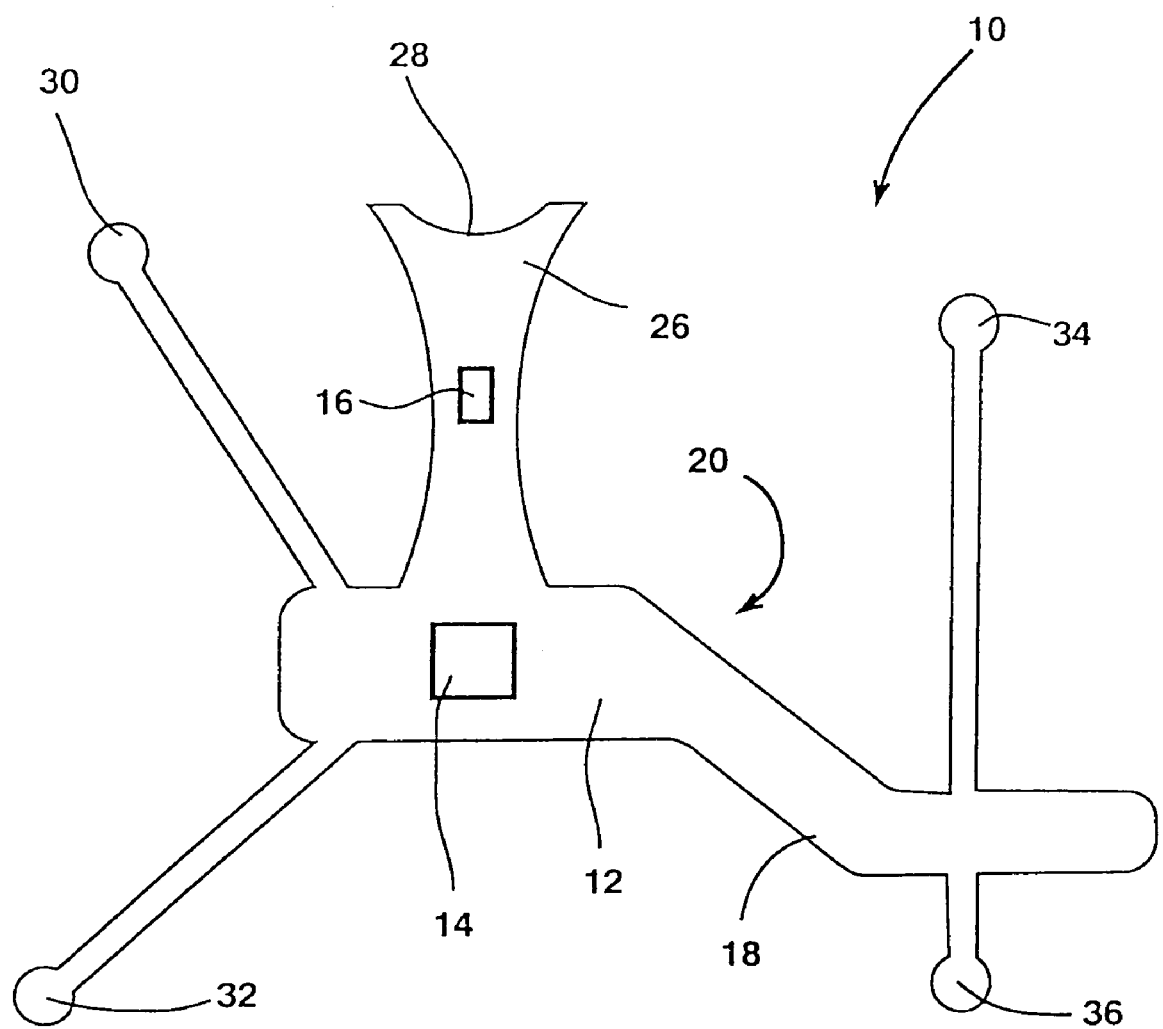
FIG. 1 is a view of the surface of the precordial pad, which would face away from the patient.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

While there is shown and described the present preferred embodiment of the invention, it is to be distinctly understood that this invention is not limited thereto but may be variously embodied to practice within the scope of the following claims.

Several preferred embodiments of the invention are shown in FIGS. 1-12. FIG. 1 shows a disposal EKG precordial pad of the invention, which is designated as 10. This embodiment of the invention includes a pad body 12, which includes a sliding site for module attachment 14 and a temperature window 16. The pad body includes an outer surface 18 and a body surface 20. FIG. 1 is a view of the outer surface, with the body surface 20 being located on the opposite side of this view of the pad body 12. In this view of the precordial pad body 10, the embedded electrodes are not visible. A data-transmitting module 22 interfaces with the sliding site for module attachment 14. This will be discussed further in other figures. A temperature sensor 24 is also present in the device, with data from the temperature sensor 24 being displayed in the temperature window 16. The precordial pad 10 includes a positioning extension 26. In the embodiment shown in FIG. 1, the position extension 26 is attached to the pad body 12. Other embodiments of the device could include a positioning extension 26 which is detachable or not attached at all, to the pad body 12.

A doctor, technician or any professional or non-professional user uses the positioning extension 26 on a patient to determine the correct placement of the precoridal pad 10. The positioning extension 26 includes a supra sternal notch 28. The supra sternal notch 28 is meant to be placed adjacent the manubrium, which is the bone adjacent to the jugular notch directly above the ribcage and at a patient's throat. By placing the supra sternal notch 28 of the precordial pad 10 adjacent the jugular notch of the patient, the electrodes of the precordial pad are assured of being placed in the proper anatomical position on a patient. Also included in the precordial pad 10, shown in FIG. 1, is an upper right limb lead 30. Although this is on the left hand side of FIG. 1, it would be associated with the patient's right side. Also, in the embodiment in FIG. 1 is a lower right limb lead 32, an upper left limb lead 34, and a lower left limb lead 36.

Figure 2:
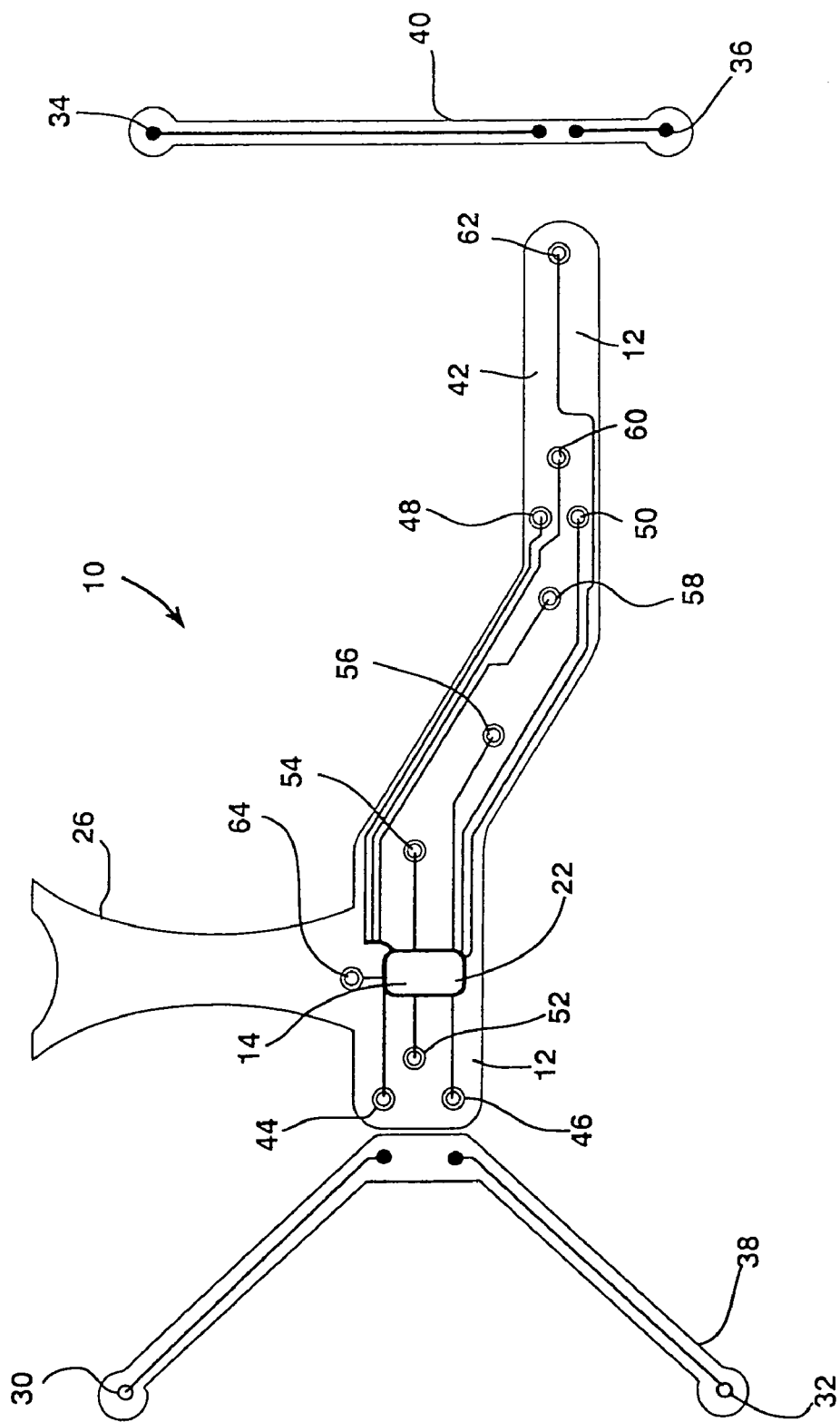
FIG. 2 is a view of the circuit layer of the precordial pad, with detachable limb leads.

Shown in FIG. 2 is another favored embodiment of the invention. In this embodiment, the limb leads are available as attachments to the pad body 12. This embodiment includes a right limb lead assembly 38 and a left limb lead assembly 40. The embodiment shown in FIG. 2 shows the circuit layer 42 of the pad body 12. In the circuit layer 42, the electrical connections which are associated with each electrode are visible. The electrodes include an upper right limb lead connection 44 and a lower right limb lead connection 46, to which the upper right limb lead 30 and the lower right limb lead 32 are connected when the right limb lead assembly 38 is attached to the pad body 12. The electrical connections would be sufficient to carry higher voltages if to be used with a defibrillation option. In such a case, only certain predetermined electrodes would be used for defibrillation.

Similarly, an upper left limb lead connection 48 is provided, as well as a lower left limb lead connection 50. These are provided so that a connection can be made with the upper left limb lead 34 and the lower left limb lead 36, which are part of the left limb lead assembly 40. These limb lead assemblies 38 and 40 can optionally be snapped into place, or the pad body may be used without limb leads. Electrode 52 is the V1 electrode, electrode 54 is the V2 electrode, the electrode 56 is the V3 electrode, electrode 58 is the V4 electrode, electrode 60 is the V5 electrode, and electrode 62 is the V6 electrode. The positions of these electrodes, V1 through V6, correspond to known electrode geometries and provide an accurate EKG reading when positioned on the patient's body correctly.

As in FIG. 1, the embodiment of FIG. 2 includes a positioning extension 26. As can be seen in FIG. 2, electrical connection between each of the electrodes is made with the module attachment site 14. A data-transmitting module 22, not shown in FIG. 2, is utilized to transmit the data from each of the electrodes to the EKG machine. Electrode 64 is provided to obtain a temperature reading, which is conveyed to the site for module attachment 14 and to the data-transmitting module 22.

Figure 3:
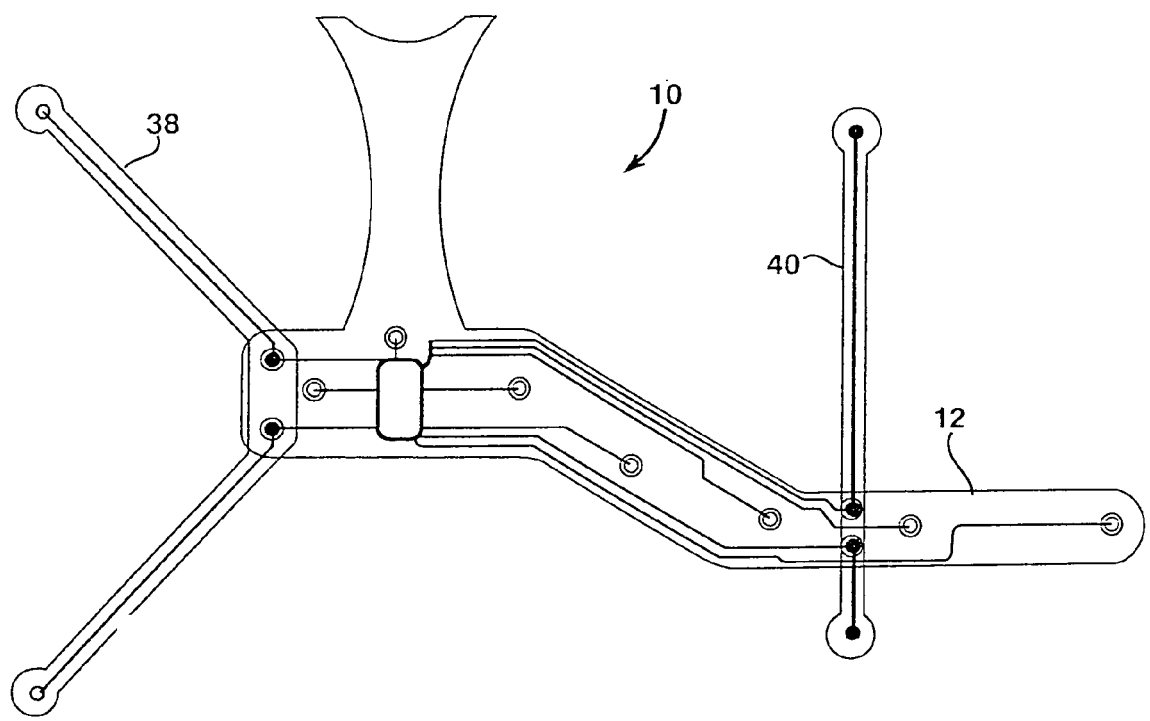
FIG. 3 is a view of the circuit layer of the precordial pad with detachable limb leads in the attached position.

FIG. 3 shows the right limb lead assembly 38 and the left limb lead assembly 40 attached in place on the pad body 12, showing the circuit layer 42.

Figure 4:
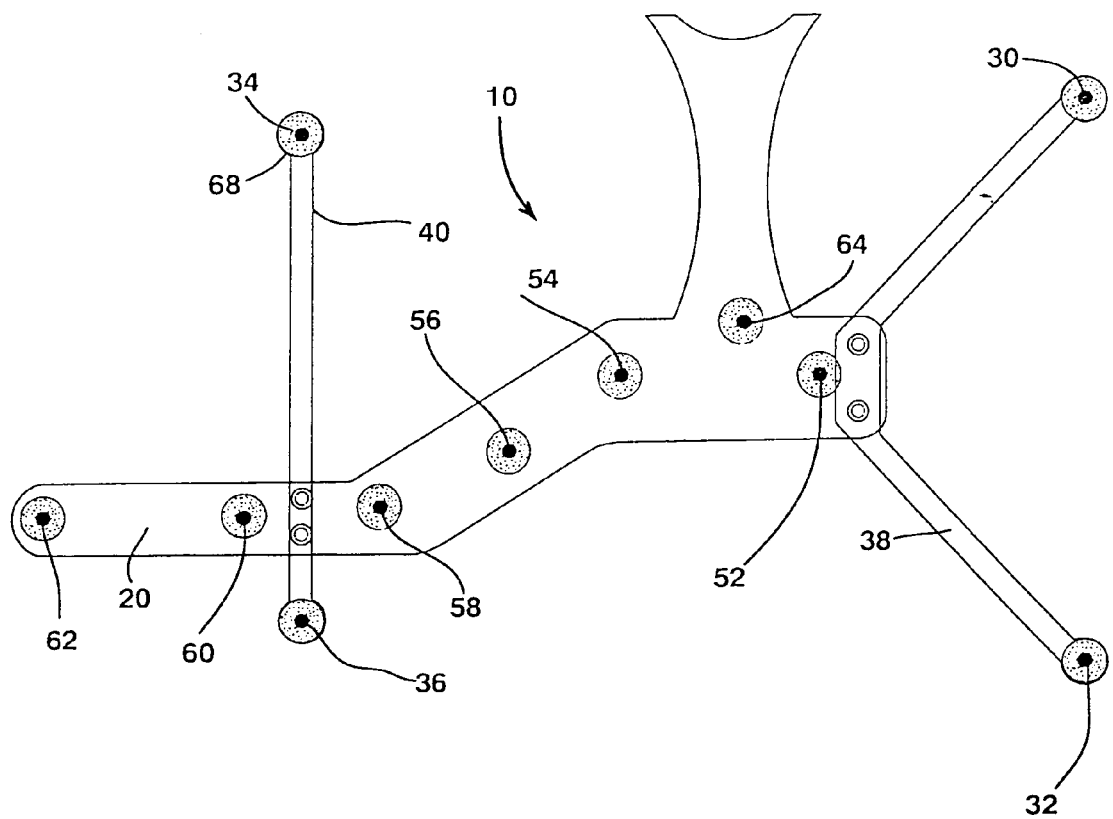
FIG. 4 is a view of the precordial pad with limb leads attached, showing the surface which contacts the patient.

The embodiment shown in FIG. 4 is the same as that in FIG. 3. However, what is shown is the body surface of the pad body, also called the body surface layer. This is the view of the device, as it would contact the patient's body. The electrodes 52, 54, 56, 58, 60, 62, and 64 are shown. They are connected by the electrical connection shown in FIG. 3, which is not visible in this view. The right and left limb lead assemblies 38 and 40 are shown in their attached configuration, attached to the connections 44, 46, 48, and 50. Shown around each electrode is a zone of adhesive material. Adhesive material may also optionally be placed on the pad body 12 in various locations.

Figure 5:
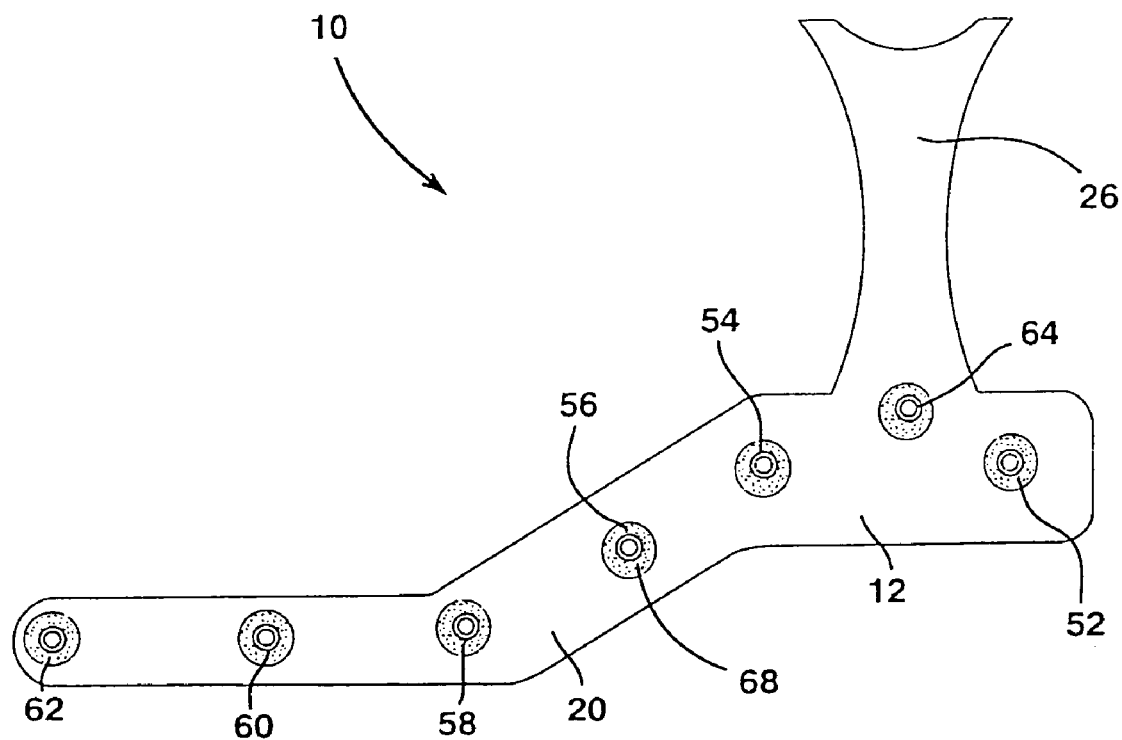
FIG. 5 is a view of the precordial pad that does not have limb leads, showing the side which contacts the patient.

FIG. 5 is a view of the second surface 20 of the pad body, the surface which contacts the patient's skin. This version of the device does not have the right or left limb lead assembly, and shows an optional configuration of the precordial pad 10.

Figure 6:
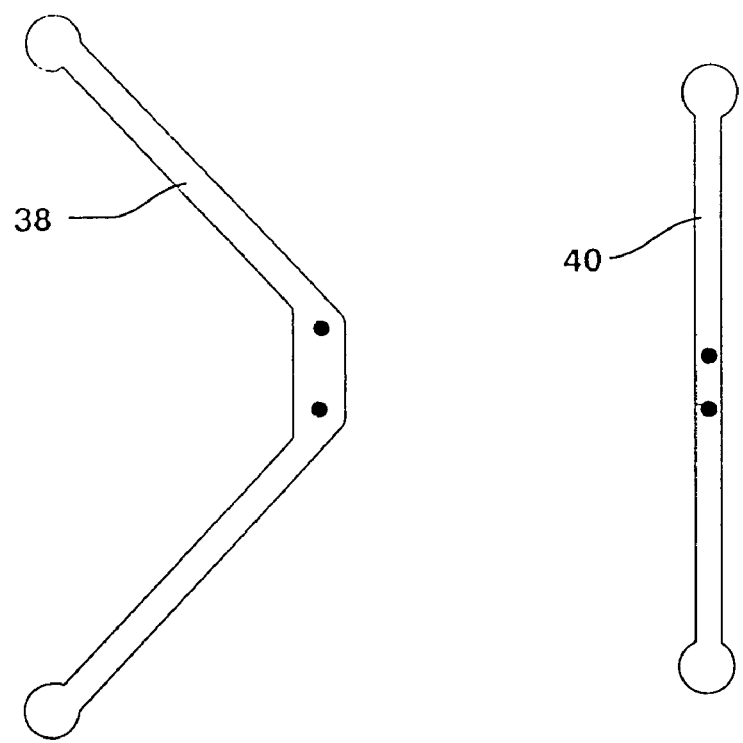
FIG. 6 is a view of the attachable limb leads.
Figure 7:
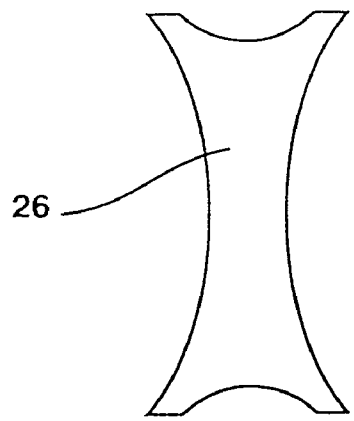
FIG. 7 is a view of a positioning device detached from the pad.

FIG. 6 shows view of the right limb lead assembly 38 and the left limb lead assembly 40, which may be optionally used with the versions of the precordial pad 10 which are shown in FIGS. 2-4. FIG. 7 shows the positioning extension 26 which can be detachable from, or used as a separate piece with the precordial pad 10.

Figure 8:
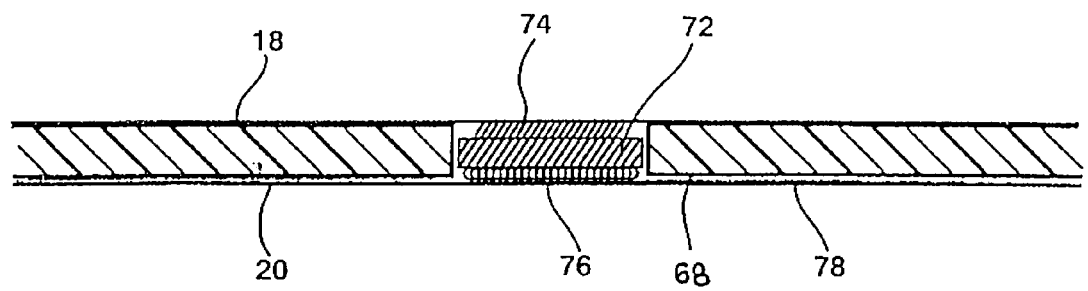
FIG. 8 is a view of the electrodes in closed and opened positions.
Figure 8:
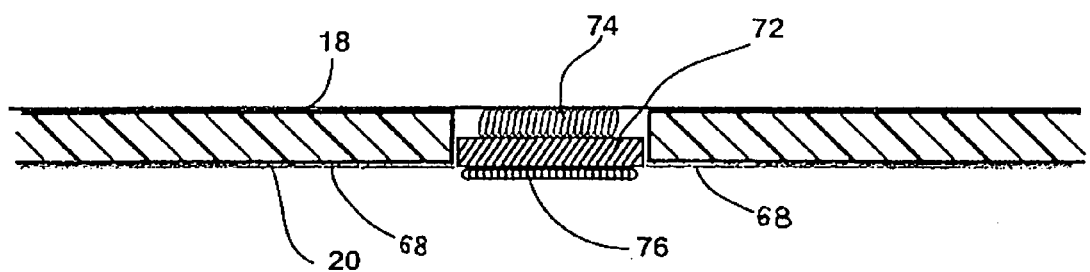

FIG. 8 shows a cross-sectional and enlarged view of an electrode 72 in the precordial pad. Also shown, are the first surface of the pad body 18 and the second surface of the pad body 20. The second surface of the pad body 20 would be positioned against the skin of the patient. Between the electrode 72 and the first surface 18, is a biased member 74. The biased member 74 is a device which is stored under some degree of compression and, when released, expands and causes the electrodes 72 to move away from the first surface 18. The biased member 74 can be a spring, such as a coil spring, or it can be a compressible substance such as foam. When released, either the spring or the foam would expand and cause the electrode 72 to move away from the first surface 18. On the electrode 72, the surface opposite the biased member 74 is a conductive gel 76. The conductive gel 76 is added to the surface of the electrode 72 during manufacture. On the second surface 20 a layer of adhesive 68 is located. A cover layer 78 covers the adhesive 68. When the cover layer 78 is removed, as shown in the lower corner of FIG. 8, the biased member 74 expands and pushes the electrode 72 away from the first surface 18. Removal of the cover layer 78 exposes the adhesive surface 68 and the gel 76.

Figure 9:
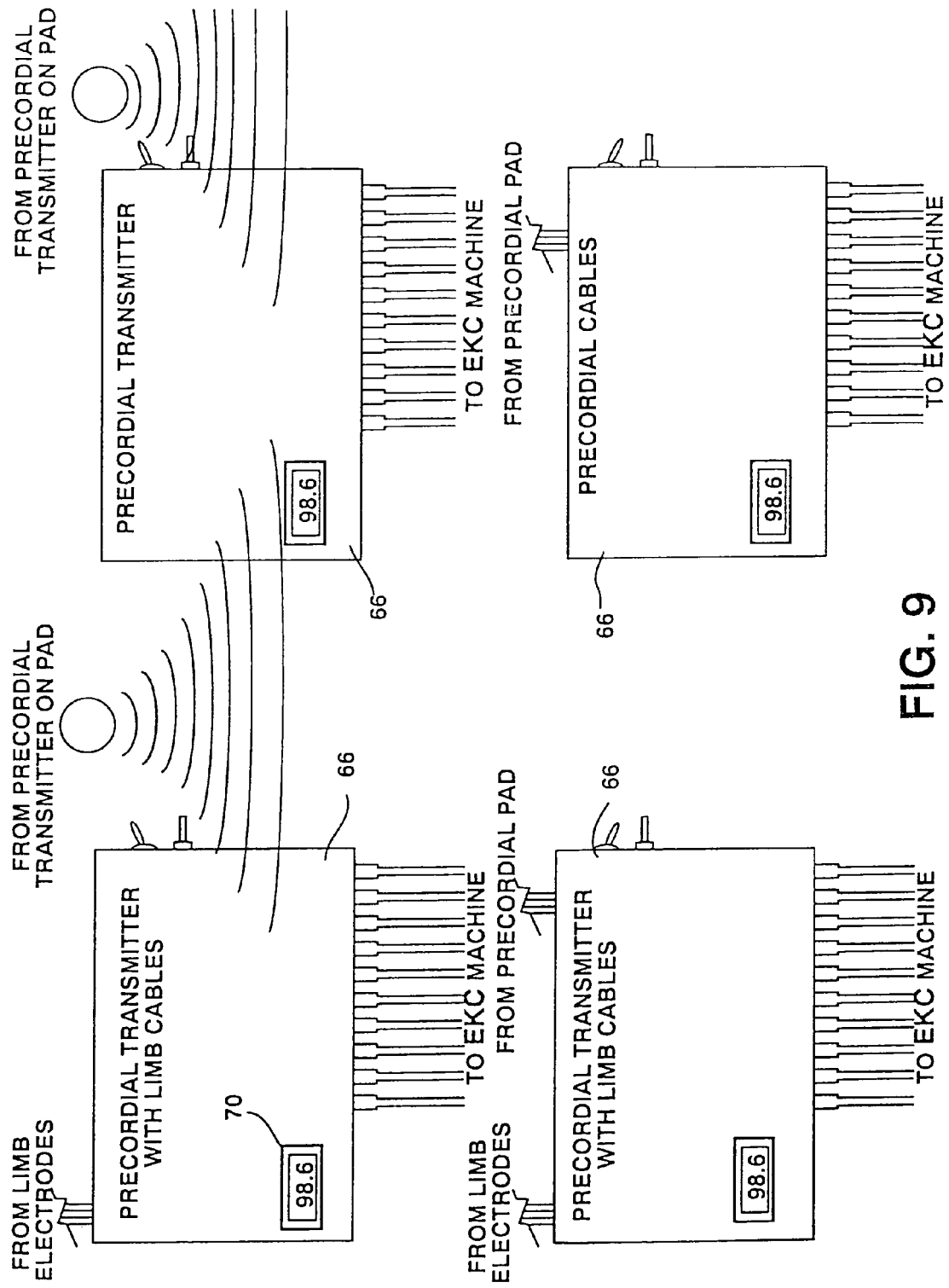
FIG. 9 shows various configurations of the universal adaptor.

FIG. 9 shows a number of configurations by which the EKG system of the invention would transmit information to any EKG machine. Shown in FIG. 9 is the universal adaptor/receiver of the accessory system. The universal adaptor/receiver is numbered 66. The universal adaptor can take several configurations, which are shown in FIG. 9. In the upper left corner of FIG. 9 is an example of the adaptor/receiver 66 of the invention configured for wireless reception of information from electrodes from the precordial pad. It is also configured for hardwired input of data from the limb electrodes. Shown on the adaptor/receiver 66 is a temperature window 70, which is a separate window from the temperature window 16, which is located on the precordial pad. From the adaptor/receiver 66, wires extend to the EKG machine. From the foregoing description, it will be apparent that various changes may be made without departing from the spirit and scope of the invention as defined by the following claims.

In the lower left corner of FIG. 9 is a depiction of a universal adaptor/receiver 66 of the invention, which is configured for hardwire transmission of data from the precordial pad and from the limb electrodes.

In the upper right corner of FIG. 9 is a depiction of the adaptor/receiver 66, which is configured to receive wireless transmission from both the electrodes of the precordial pad and limb electrodes.

In the lower right corner of FIG. 9 is a universal adaptor/receiver 66 configured to receive hardwired information from the electrodes of the precordial pad and wireless data from the limb electrodes. Any of these configurations of the universal adaptor/receiver 66 of the invention are possible.

Figure 10:
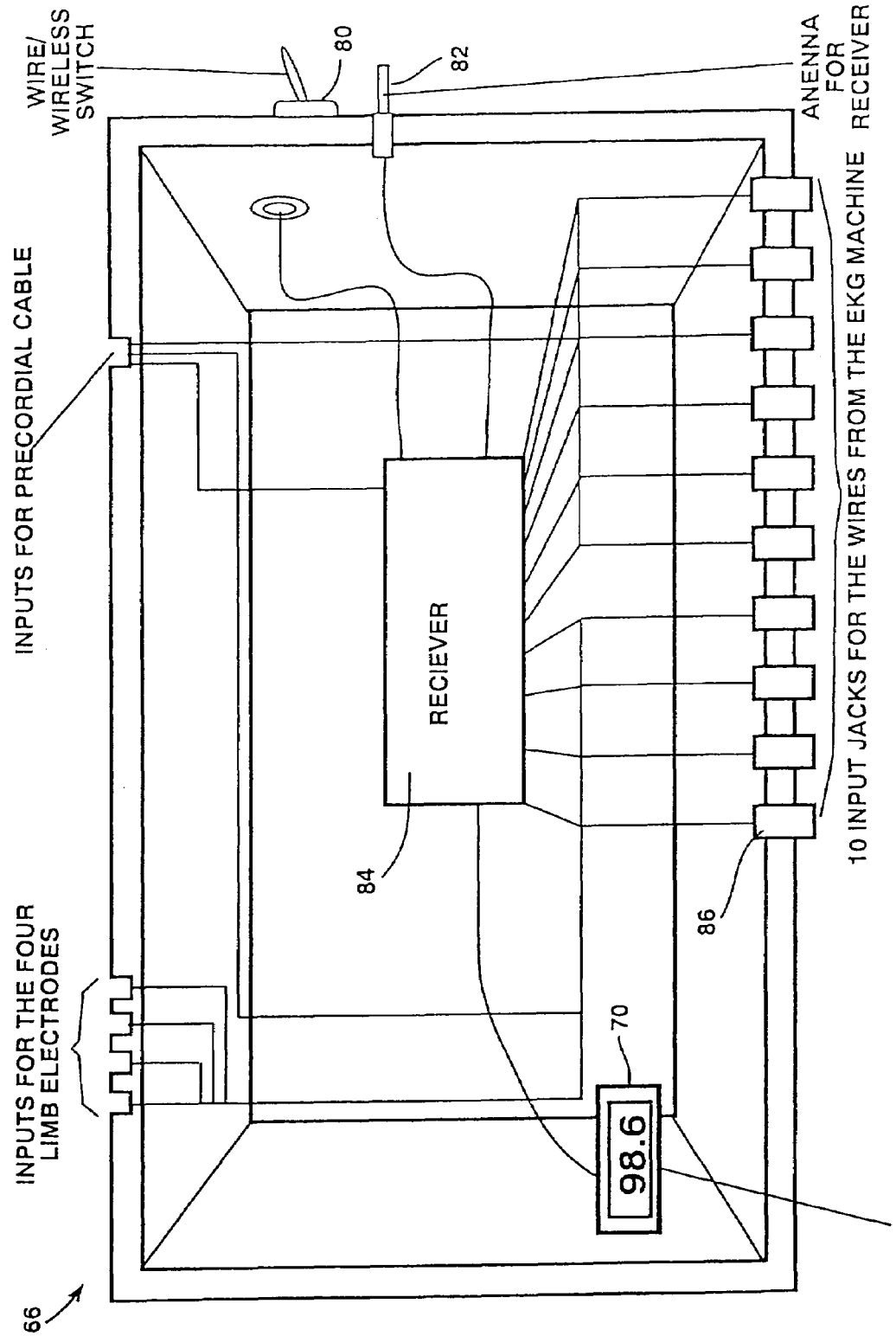
FIG. 10 shows internal structure of the universal adaptor.

FIG. 10 is a view of some of the details of the universal adaptor/receiver 66. Shown, are inputs for the four limb electrodes as well as inputs for the precordial cable. A wireless switch 80 is shown for switching the unit from wireless to wired operation. Also shown, is an antenna 82 for receiving a wireless signal from the precordial pad of the invention. The antenna 82 is connected to a receiver 84 that receives, processes, and transmits the information from the precordial pad to outlet jacks 86. Outlet jacks 86 are available for connection to the EKG machine. This would typically be by a wired connection, but using wireless technology for this connection would also be possible. Thermometer window 70 is also shown.

Figure 11:
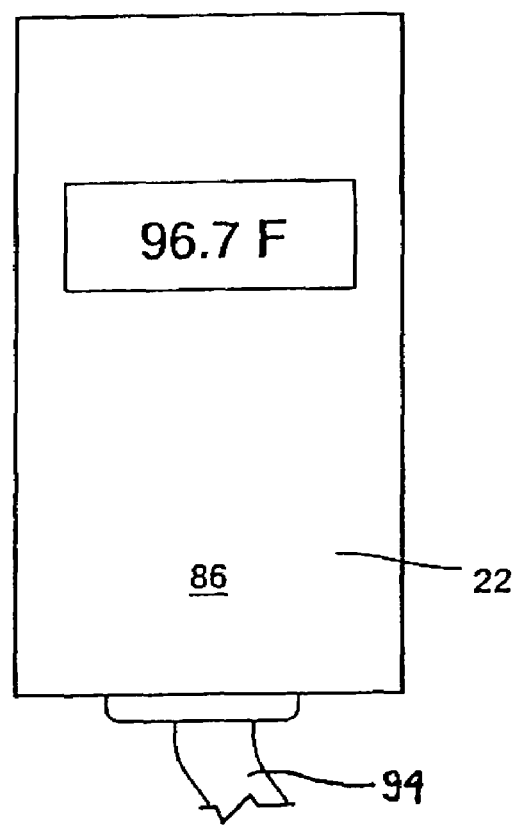
FIG. 11 is a view of the data transmitting module.
Figure 11:
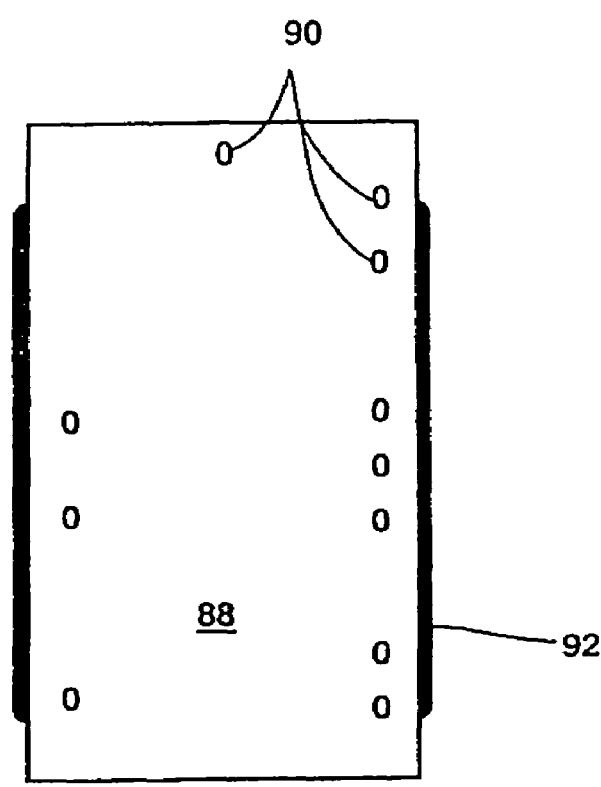

FIG. 11 shows a system transmitting module, which has also been called the signal export device 22. It has a first surface 86 and a second surface 88. The second surface 88 includes contact points 90 which provide electrical connection with the electrodes or the precordial pad. The signal export device 22 connects to the precordial pad 10 by means of the sliding site for module attachment 14. The signal export devices include sliding borders 92, which allow it to slide into a positive engagement with the sliding site for module attachment 14. Although brackets on the side of the unit are shown, attachment could be accomplished by a number of configurations, as are well known in the industry. This unit could be operated with a cable 94 or could operate by wireless transmission.

Figure 12:
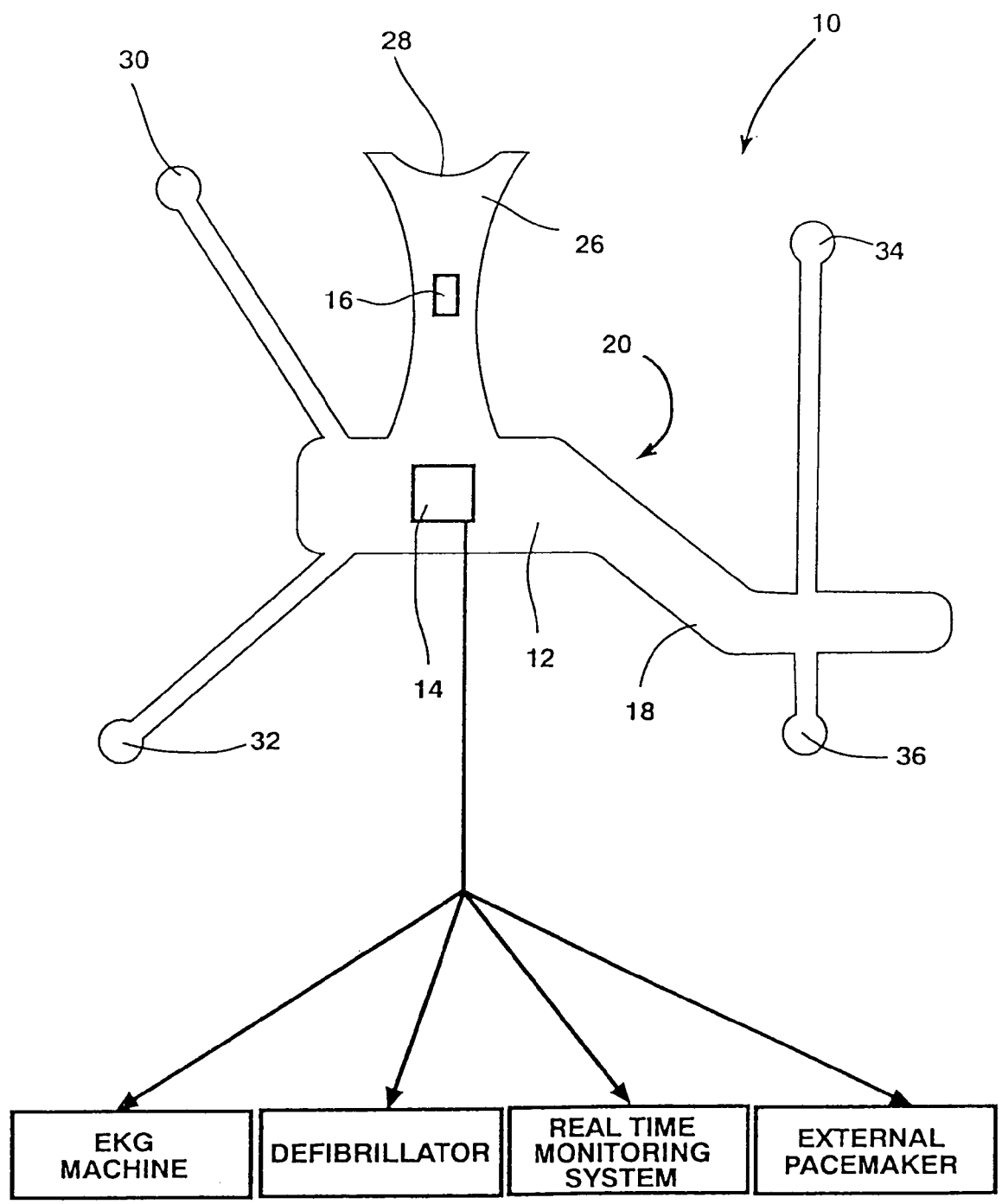
FIG. 12 shows the pad of the invention with optional attachment to an EKG machine and selected non-EKG devices.

FIG. 12 shows a pad of the invention and possible connections with which it can be used. These include an EKG machine, a defibrillator, a real time heart monitoring system, and an external heart pacing machine.

I claim:

1. An EKG recording accessory system, which comprises:
a selection of disposable precordial pads in different sizes, with attached positioning devices, for use in accurately positioning a said pad;
a universal adaptor/receiver which is compatible for connection to all EKG recording and monitoring machines, for receiving data from said electrodes and transferring data to an EKG machine from said precordial pad, and for connection to non-EKG devices, including defibrillators, real time heart monitors, and external pacemakers;

each of said precordial pads comprising
a pad body for conductive attachment to a patient's torso, said pad body having an outer surface and a body surface;
an adhesive surface on said body surface for contact with said patient's skin;
an adhesive cover, which is removable for exposing said adhesive surface before use;
a plurality of electrodes embedded in said pad body and extending from said pad body for electrical connection to the patient's torso, said embedded electrodes having an electrode extension device, for causing said electrodes to extend beyond said adhesive surface when said adhesive cover is removed, said electrode extension device un-extended when positively covered by said adhesive cover;
a data-transmitting module, for sending a plurality of signals from said embedded electrodes to an EKG machine; and
a temperature sensor for sensing the temperature of said patient's skin and for sending temperature information to said EKG machine.

2. The EKG recording accessory system of claim 1, in which said universal adaptor/receiver of said system further includes a temperature reading window.

3. The EKG recording accessory system of claim 1 in which said universal adaptor/receiver of said system further includes a switch to select between wireless and hardwired operation.

4. The EKG recording accessory system of claim 1 in which said data transmitting module is a wireless transmitter.

5. The EKG recording accessory system of claim 1 in which said data transmitting module is a wire cable with individual wires.

6. The EKG recording accessory system of claim 1 in which said plurality of electrodes includes one or more micro-transmitters for sending a signal from said electrode.

7. The EKG recording accessory system of claim 1 in which said disposable precordial pads further include a circuit layer which is located between said outer surface and said body surface, and which includes electronic connections between said electrodes and said data transmitting module.

8. The EKG recording accessory system of claim 7 in which said circuit layer is comprised of an insulating sheet on which is placed electrical connections in the form of conductive pathways.

9. The EKG recording accessory system of claim 8 in which said conductive pathways are in the form of metallic ink circuitry.

10. The EKG recording accessory system of claim 1, wherein said electrode extension device is a biased member mounted between said embedded electrode and said outer surface, which is held in biased position by said adhesive cover, and which moves said electrode away from said pad when said adhesive cover is removed.

11. The EKG recording accessory system of claim 10 in which said electrode extension device is a spring or spring-like device.

12. The EKG recording accessory system of claim 10 in which said biased member is a foam structure.

13. The EKG recording accessory system of claim 10 in which said embedded electrode is packaged under said adhesive cover with a layer of transmitting gel, in which said transmitting gel and said embedded electrode are exposed when said adhesive cover is removed.

14. The EKG recording accessory system of claim 1 in which said disposable precordial pads of the system further include six embedded electrodes in a predetermined geometry.

15. The EKG recording accessory system of claim 14 in which said disposable precordial pads of the system further include 4 connection points for attachment of limb electrodes.

16. The EKG recording accessory system of claim 15 in which said disposable precordial pads of the system further include 2 right heart electrodes.

17. The EKG recording accessory system of claim 1 in which said embedded electrodes in said disposable precordial pads of the system each have a micro-transmitter for wireless transmission of a signal to said data transmitting module.

18. The EKG recording accessory system of claim 1 in which said universal adaptor/receiver for an EKG recording and monitoring machine further comprises an EKG machine interface, to which wire leads from any brand of EKG may be attached, and a precordial pad interface, to which a single multi strand cable from said disposable precordial pads of the system may be attached.

19. The EKG recording accessory system of claim 18 in which said universal adaptor/receiver further comprises a receiver for receiving data from a micro-transmitter and transferring said data to an EKG recorder.

20. The EKG recording accessory system of claim 1 in which said universal adaptor/receiver further comprises a display to indicate body temperature.

21. The EKG recording accessory system of claim 1, in which said universal adaptor/receiver further includes a selection means to select between wired or wireless reception of signals.

22. The EKG recording accessory system of claim 1 in which said universal adaptor/receiver further includes an EKG machine selector function, by which a specific EKG machine may be selected for interface with said data from said disposable precordial pads.

* * * * *